(12) United States Patent
Fujii

(10) Patent No.: US 7,067,202 B2
(45) Date of Patent: Jun. 27, 2006

(54) LUMINESCENT ORGANOMETALLIC COMPOUND AND LIGHT EMITTING DEVICE

(75) Inventor: Hiroyuki Fujii, Kyoto (JP)

(73) Assignee: Sanyo Electric Co., Ltd., Osaka (JP)

( * ) Notice: Subject to any disclaimer, the term of this patent is extended or adjusted under 35 U.S.C. 154(b) by 162 days.

(21) Appl. No.: 10/170,396

(22) Filed: Jun. 14, 2002

(65) Prior Publication Data
US 2003/0040627 A1 Feb. 27, 2003

(30) Foreign Application Priority Data
Jun. 15, 2001 (JP) ............................. 2001-182507

(51) Int. Cl.
  H05B 33/14 (2006.01)
  C09K 11/06 (2006.01)
  C07D 409/00 (2006.01)

(52) U.S. Cl. ...................... 428/690; 428/917; 313/504; 546/4; 549/3

(58) Field of Classification Search ................ 428/690, 428/917; 313/504; 252/301.16; 546/4; 549/3, 59, 206, 209; 548/402; 556/7, 9, 556/13, 28, 64, 87, 136, 137, 406; 568/1, 568/12
See application file for complete search history.

(56) References Cited

U.S. PATENT DOCUMENTS

| | | | | |
|---|---|---|---|---|
| 6,780,528 B1 * | 8/2004 | Tsuboyama et al. | ........ | 428/690 |
| 6,821,646 B1 * | 11/2004 | Tsuboyama et al. | ........ | 428/690 |
| 2001/0019782 A1 * | 9/2001 | Igarashi et al. | ............ | 428/690 |
| 2002/0063516 A1 * | 5/2002 | Tsuboyama et al. | ........ | 313/504 |
| 2002/0121638 A1 * | 9/2002 | Grushin et al. | ............... | 257/40 |
| 2002/0182441 A1 * | 12/2002 | Lamansky et al. | .......... | 428/690 |
| 2003/0059646 A1 * | 3/2003 | Kamatani et al. | ........... | 428/690 |

OTHER PUBLICATIONS

U.S. Appl. No. 60/215,362.*
U.S. Appl. No. 60/224,273.*
U.S. Appl. No. 60/283,814.*
Mauro Maestri et al., "Photochemistry and Luminescence of Cylcometallated Complexes", Advances in Photochemistry, vol. 17, pp. 1-5 and 25-35 (1992).*

* cited by examiner

Primary Examiner—Marie Yamnitzky
(74) Attorney, Agent, or Firm—Kubovcik & Kubovcik

(57) ABSTRACT

A luminescent organometallic compound having the chemical structure represented by the general formula (1) or (2):

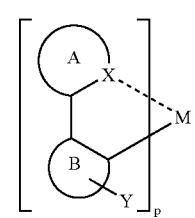

(1)

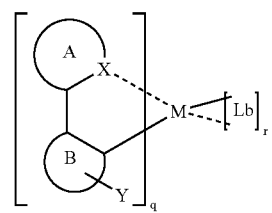

(2)

[in the general formulas (1) and (2), A and B represent ring structures, M represents a metallic atom, X represents a hetero atom other than carbon and hydrogen, Y represents at least one electron-attracting group connecting to ring structure B, Lb represents a unidentate or multidentate ligand, and p, q and r represent positive integers.]

2 Claims, No Drawings

LUMINESCENT ORGANOMETALLIC COMPOUND AND LIGHT EMITTING DEVICE

BACKGROUND OF THE INVENTION

1. Field of the Invention

The present invention relates to an organometallic compound having an excellent luminous efficiency and capable of emitting light of spectrum components of red or blue wavelength band, and to a light emitting device such as organic electroluminescent device using the same.

2. Related Art

As the recent development of information technology (IT), there have been increased needs for low-profile display devices having a small thickness of about several millimeters and capable of achieving full color display. Approaches to realize the full color display can be generally classified into three types of methods: (1) arranging a number of light emitting devices which respectively emit monochromatic light of red, green and blue which are the primary colors of light; (2) using white light emitting devices in combination with color filter which allow monochromatic light of primary colors to pass through; and (3) using light emitting devices which emit ultraviolet light or blue light in combination with wavelength converting means for converting the above light into monochromatic light of the primary colors of light.

As such a display apparatus which is capable of full-color display according to the above method (1), display apparatuses using a electroluminescent device are known. As such an electroluminescent device, inorganic electroluminescent devices using inorganic substances such as sulfates as a light emitting material. Since an inorganic electroluminescent device requires high driving voltage and hence requires AC driving, it becomes difficult to increase the reliability of peripheral driving circuits and hence the cost will increase. Furthermore, since it is driven by high AC voltage, strong electromagnetic waves are radiated, which posed a problem that an adverse effect could be exerted on peripheral electronic devices.

In recent years, for realizing low-profile light emitting devices wherein the above-mentioned problems are solved, organic electroluminescent devices using amorphous thin films made of organic substances as light emitting materials have been enthusiastically developed.

It is generally considered that a green light emitting device can be realized in a relatively easy manner with high performance, while it is difficult to realize a blue or red low-profile light emitting device. Also, in the cases of organic electroluminescent devices, devices that can emit light of spectrum components of a blue or red wavelength band are desired.

Forrest, Stephen R. et al. disclosed in Appl. Phys, Lett., 1999, 75(1), 4–6, an organic electroluminescent device using a mixture light emitting layer in which tris(2-phenylpyridine) iridium (Ir(ppy)), which is green iridium (Ir(ppy)), which is green phosphorescence luminescent substance, is mixed into 4,4'-bis(carbazole-9-yl)-biphenyl (CBP) in a concentration of 1 to 12% wt. In such a light emitting device, a light emission peak which is considered as coming from the triplet excited state of Ir(ppy) is observed, and an excellent luminous efficiency is obtained.

Those capable of emitting light from the triplet excited state as described above emit light via the triplet excited state that is not usually involved in light emission and thus is not utilized effectively, so that the luminous efficiency can be significantly improved. For this reason, also for red or blue light emission, organic electroluminescent devices that are capable of emitting light via the triplet excited state even are requested.

SUMMARY OF THE INVENTION

It is an object of the present invention to provide a luminescent organometallic compound having an excellent luminous efficiency and capable of emitting red or blue light, and to provide a light emitting device using the same.

A luminescent organometallic compound according to the present invention is characterized by having the chemical structure represented by the general formula (1) or (2) as follows:

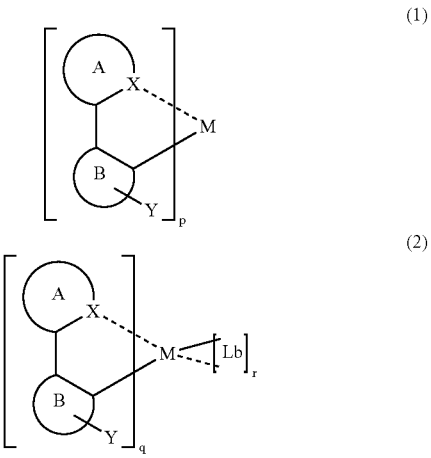

[in general formulas (1) and (2), A and B represent ring structures, M represents a metallic atom, X represents a hetero atom other than carbon and hydrogen, Y represents at least one electron-attracting group bonding to ring structure B, Lb represents a unidentate or multidentate ligand, and p, q and r represent positive integers.]

In the above general formulas (1) and (2), it is preferred that A and/or B exhibit(s) an aromatic property. Furthermore, provided that the number of π electrons of aromatic ring A is 4m+2 (m is a positive integer) and the number of π electrons of aromatic ring B is 4n+2 (n is a positive integer), it is preferred that m is larger than n.

The bond between hetero atom X and metallic atom M may be a covalent bond or a coordinate bond, with the coordinate bond being preferred in general.

It is preferred that hetero atom X is an element which is higher in electronegativity than carbon, and is an element selected from, for example, nitrogen, oxygen, sulfur, boron, silicon, germanium, phosphorus, arsenic, selenium, tellurium, fluorine, chlorine, bromine and iodine. Nitrogen, oxygen or sulfur is particularly preferred.

Metallic atom M is preferably an element having an atomic number of not less than 56, and more preferably an element having an atomic number of not less than 75. To be more specific, at least one element selected from tungsten, rhenium, osmium, iridium, platinum and gold is particularly preferred.

Substituent Y bonding to ring structure B is not particularly limited so far as it is a substituent that exhibits higher electron attractivity than hydrogen, and examples of which include a halogen, a cyano group; or an alkyl group, phenyl group or aryl group substituted by a halogen or a cyano group.

A luminescent organometallic compound according to the present invention is exemplified by an organometallic compound having the chemical structure represented by any of the following general formulas (3) to (10):

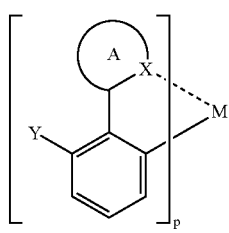
(3)

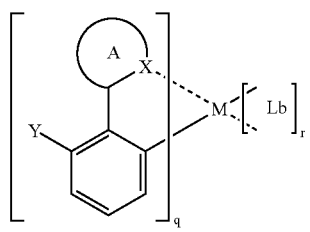
(4)

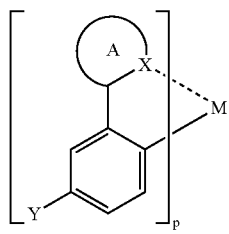
(5)

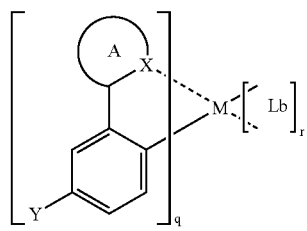
(6)

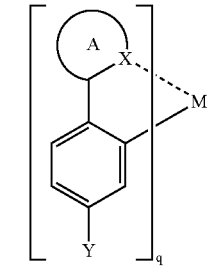
(7)

-continued

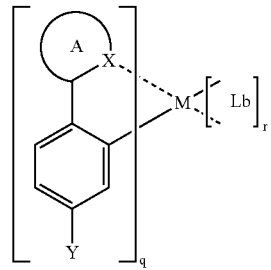
(8)

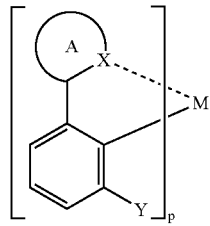
(9)

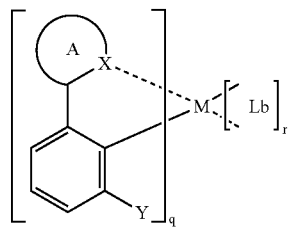
(10)

[in the general formulas (3) to (10), A represents a ring structure, M represents a metallic atom, X represents a hetero atom other than carbon and hydrogen, Y represents an electron-attracting group bonding to the phenyl ring, Lb represents a unidentate or multidentate ligand, and p, q and r represent positive integers.]

A luminescent organometallic compound according to the present invention is exemplified by an organometallic compound having the chemical structure represented by any of the following general formulas (11) to (14):

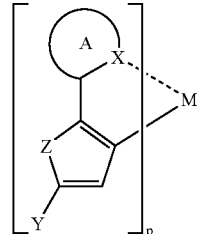
(11)

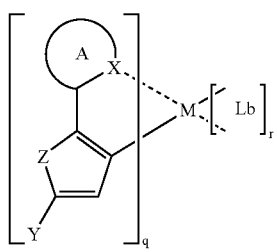
(12)

-continued (13)

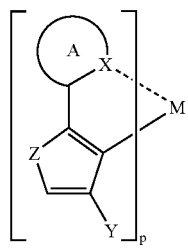

(14)

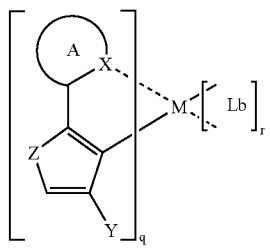

[in the general formulas (11) to (14), A represents a ring structure, M represents a metallic atom, X and Z represent hetero atoms other than carbon and hydrogen, which may be different from each other, Y represents an electron-attracting group bonding to the hetero ring, Lb represents a unidentate or multidentate ligand, and p, q and r represent positive integers.]

A luminescent organometallic compound according to the present invention is exemplified by an organometallic compound having the chemical structure represented by any of the following general formulas (15) to (18):

(15)

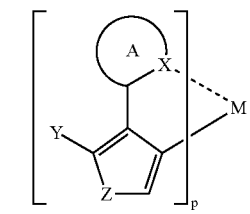

(16)

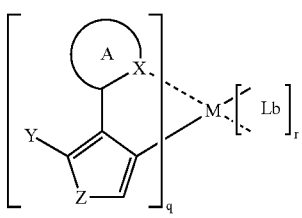

(17)

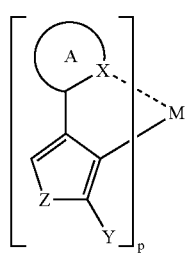

(18)

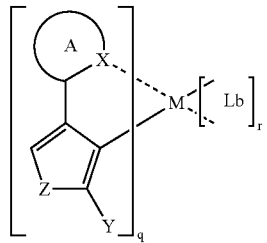

[in the general formulas (15) to (18), A represents a ring structure, M represents a metallic atom, X and Z represent hetero atoms other than carbon and hydrogen, which may be different from each other, Y represents an electron-attracting group bonding to the hetero ring, Lb represents a unidentate or multidentate ligand, and p, q and r represent positive integers.]

A luminescent organometallic compound according to the present invention is exemplified by an organometallic compound having the chemical structure represented by any of the following general formulas (19) to (22):

(19)

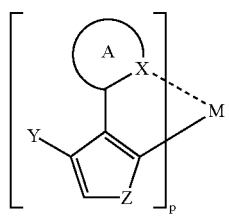

(20)

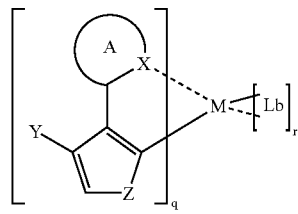

(21)

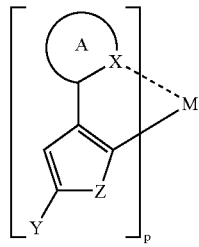

(22)

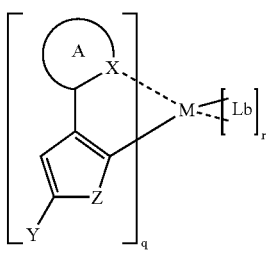

[in the general formulas (19) to (22), A represents a ring structure, M represents a metallic atom, X and Z represent hetero atoms other than carbon and hydrogen, which may be different from each other, Y represents an electron-attracting group bonding to the hetero ring, Lb represents a unidentate or multidentate ligand, and p, q and r represent positive integers.]

In the above general formulas (3) to (22), it is preferred that A exhibits an aromatic property. Furthermore, it is preferred that the number of π electrons of aromatic ring A is 4m+2 (m is a positive integer).

It is preferred that hetero atom Z is an element which is higher in electronegativity than carbon, and is an element selected from, for example, nitrogen, oxygen, sulfur, boron, silicon, germanium, phosphorus, arsenic, selenium, tellurium, fluorine, chlorine, bromine and iodine. Nitrogen, oxygen or sulfur is particularly preferred. The hetero atom Z may be identical to or different from hetero atom X.

It is preferred that the luminescent organometallic compound according to the present invention emits spectrums of blue or red wavelength band. Furthermore, it is preferred that the luminescent organometallic compound according to the present invention emits light via the triplet excited state. Furthermore, it is preferred that the luminescent organometallic compound according to the present invention has sublimability or is volatile. Those having sublimability can form a thin layer of a luminescent organometallic compound by vapor deposition or vacuum deposition.

A luminescent organometallic compound according to another aspect of the present invention is a luminescent organometallic compound including a first structural moiety having a bond between a carbon atom and a metallic atom and a second moiety having a bond between a hetero atom other than carbon and hydrogen and said metallic atom, wherein at least one hydrogen of the first structural moiety is substituted by an electron-attracting group.

In the luminescent organometallic compound of the above aspect, it is preferred that the first structural moiety and/or the second structural moiety form(s) an aromatic ring. Further, it is preferred that the bond between the hetero atom and the metallic atom in the second structural moiety is a coordinate bond.

A light emitting device according to the present invention is characterized in that the above-mentioned luminescent organometallic compound according to the present invention is included in a light emitting layer arranged between a pair of electrodes.

Examples of lamination structure of the light emitting device include: a lamination structure in which anode/hole transporting layer/light emitting layer/hole blocking layer/cathode are arranged in this order and a lamination structure in which anode/hole injection layer/hole transporting layer/light emitting layer/hole blocking layer/electron injection layer/cathode are arranged in this order.

In the luminescent organometallic compound according to the present invention, since at least one electron-attracting group Y bonds to ring structure B, the electron density at the carbon bonding to metallic atom M is reduced, and the effective electronegativity of the carbon increases. As a result of this, the bond between metallic atom M and the carbon becomes strong, resulting in increased chemical stability of the organometallic compound.

When quantum-mechanically considering the light emitting process of the light emitting material, by passage of electric current, among all of the excited states generated by coupling between an electron and a hole, the triplet excited state wherein the electron spin is parallel occurs in a ratio of three-fourth, while the singlet excited state wherein the electron spin is antiparallel and a sum of spin quantum numbers is zero occurs in a ratio of one-fourth. Of these two kinds of excited states, a light emitting phenomenon caused by an electron in the singlet excited state transiting to the ground state is referred to as fluorescence. Fluorescence is spin-allowed. In other words, since fluorescence does not need to involve inversion of electron spin, it can easily happen. Therefore, fluorescence is widely utilized in light emitting phenomena such as fluorescent materials and organic electro-luminescence.

On the other hand, light emission caused by an electron in the triplet excited state transiting to the ground state is referred to as phosphorescence. Phosphorescence is spin-forbidden. According to the Pauli exclusion principle, since two electrons of which electron spins are parallel with each other never exist on the same electron orbital (in this case, corresponding to the ground state), in order for an electron to transit to the ground state to emit light, it is necessary that the electron spin of the transiting electron inverses in response to some perturbation. Most of fluorescent materials and materials usually used for organic electroluminescence have difficulties in spin inversion. Therefore, phosphorescence is known as a special phenomenon which is observed only in extreme low temperature regions of not more than the liquid nitrogen temperature in limited substance.

According to the luminescent organometallic compound of the present invention, since the perturbation that the electron spin of the transiting electron receives, or the interaction between the spin and the orbital becomes large, light emission via the triplet excited state can be measurably observed. Therefore, light emission is enabled via the triplet excited state that is not responsive for light emission and thus was not effectively utilized, so that it is possible to significantly improve the luminous efficiency.

A luminescent organometallic compound according to the present invention can be produced by allowing a first material supplying metallic atom M and a second material supplying an organic compound to be bonded to organic metallic atom M to react with each other.

As the first material, a metal complex of metallic atom M can be used. The oxidation number of metallic atom M is preferably 0 to 3. As metallic atom M, tungsten, rhenium, osmium, iridium, platinum, gold and the like are preferably used, as described above. The most preferred oxidation numbers for the respective metals are, for example, tungsten (0), rhenium (I), osmium (II), iridium (III), platinum (II) and gold (I).

As a ligand of a metal complex, β-diketonate group which is a bidentate ligand, picolinic acid, N-methylsalicylimine and the like are preferred. As a β-diketonate group, an acetylacetonate group is generally used, however, it is also possible to use an acetylacetonato group substituted by a substituent such as phenyl group as is necessary. As the first material, a metal complex is preferably used as described above, however, a metal chloride or a carbonyl complex having a corresponding oxidation number may be used in place of the metal complex.

As the second material, an organic compound capable of bonding to metallic atom M in the general formulas (1) and (2) is used. That is, an organic compound having ring structure s A and B and hetero atom X, as well as having electron-attracting group Y bonding to ring structure B is used.

The organic compound molecule used as the second material is substituted by an electron-attracting group, and examples of the organic compound molecule before substituted by the electron-attracting group include: 1,7-phenanthroline, 2-phenylquinoline, benzo[h]quinoline, 4-phenylpyrimidine, 2-(1-naphthyl)pyridine, 2-(2-naphthyl)pyridine, 2-phenylpyridine, 2-(thiophene-2'-yl)pyridine, 2-(benzothiophene-2'-yl)pyridine, 2-phenyloxazole, 2-phenyl(benzoxazole), 2-(1-naphthyl)benzoxazole, 2-(2-naphthyl)benzoxazole, 2-phenylthiazole, 2-phenyl(benzothiazole), 2-(1-naphthyl)benzothiazole, 2-(2-naphtyl)benzothiazole, 2-(thiophene-2'-yl)thiazole, 2-(thiophene-2'-yl)benzothiazole, 2-(benzothiophene-2'-yl)benzothiazole, 2-(1-naphthyl)quinoline, 2-(2-naphytl)quinoline and the like. Those obtainable by coupling an electron-attracting group to these compounds can be used as an organic compound molecule serving as the second material.

Examples of an organic compound molecule in which an electron-attracting group is bonded to a basic frame of 2-phenylpyridine include: 2-(2-fluorophenyl-1-yl)-pyridine, 2-(3-fluorophenyl-1-yl)-pyridine, 2-(4-fluorophenyl-1-yl)-pyridine;

2-(2,3-difluorophenyl-1-yl)-pyridine, 2-(2,4-difluorophenyl-1-yl)-pyridine, 2-(2,5-difluorophenyl-1-yl)-pyridine, 2-(3,4-difluorophenyl-1-yl)-pyridine, 2-(3,5-difluorophenyl-1-yl)-pyridine, 2-(4,5-difluorophenyl-1-yl)-pyridine;

2-(2,3,4-trifluorophenyl-1-yl)-pyridine, 2-(2,3,5-trifluorophenyl-1-yl)-pyridine, 2-(2,4,5-trifluorophenyl-1-yl)-pyridine, 2-(3,4,5-trifluorophenyl-1-yl)-pyridine; 2-(2,3,4,5-tetrafluorophenyl-1-yl)-pyridine;

2-(2-trifluoromethylphenyl-1-yl)-pyridine, 2-(3-trifluoromethylphenyl-1-yl)-pyridine, 2-(4-trifluoromethylphenyl-1-yl)-pyridine and the like.

By reaction of the first material with the second material, the whole or a part of the ligands in the first material are substituted by the second material, with the result that a luminescent organometallic compound according to the present invention as shown by the above general formulas (1) and (2) can be obtained. Ligand Lb in the general formula (2) may be a ligand kept unsubstitued in the metal complex of the first material.

As a reaction solvent used in synthesis of the luminescent organometallic compound according to the present invention, those having high polarity and high boiling point are preferred. Preferred examples of the reaction solvent include: 1,2-dinitrobenzene (boiling point(b.p.) not less than 300° C.), 1,3-dinitrobenzene (b.p. 297° C.), glycerol (1,2,3-propanetriol, b.p. 290° C.), diethylene glycol (2,2'-oxybisehtanol, b.p. 244° C.), 1,2,3-trichlorobenzene (b.p. 218° C.), 1,2,4-trichlorobenzene (b.p. 214° C.), nitrobenzene (b.p. 210° C.), ethylene glycol (1,2-ethanediol, b.p. 197° C.), dimethyl sulfoxide (b.p. 189° C.), propylene glycol (1,2-propanediol, b.p. 187° C.), 1,2-dichlorobenzene (b.p. 180° C.), N,N-dimethylformamide (b.p. 153° C.), ethylene glycol monoethyl ether (2-ethoxy ethanol, b.p. 136° C.), chlorobenzene (b.p. 132° C.), 1,4-dioxane (b.p. 101° C.), ethanol (b.p. 78° C.), tetrahydrofuran (b.p. 66° C.), water and mixtures thereof.

Examples of the organometallic compound according to the present invention include organometallic compounds having the structures shown by (Chemical Formula 45) to (Chemical Formula 56) below.

Chemical Formula 45: tris(2-(3,5-difluorophenyl-1-yl)-pyridinato-N,C$^{2'}$) iridium(III)

Chemical Formula 46: bis(2-(7-fluorobenzothiophene-2'-yl)-pyridinato-N,C$^{2'}$)acetylacetonato iridium (III)

Chemical Formula 47: tris(2-(4-fluorophenyl-1-yl)-pyridinato-N,C$^{2'}$) rhenium(III)

Chemical Formula 48: tris(2-(5-fluorothiophene-2$^1$-yl)-pyridinato-N,C$^{2'}$) iridium(III)

Chemical Formula 49: tris(2-(4-fluorophenyl-1-yl)-1,3-oxazolato-N,C$^{2'}$) iridium(III)

Chemical Formula 50: bis(2-(6-cyanonaphthalene-2-yl)benzothiazolato-N,C$^{2'}$)acetylacetonato iridium(III)

Chemical Formula 51: bis(7-fluorobenzo[h]quinolinato-N,C$^{10}$)acetylacetonato iridium(III)

Chemical Formula 52: bis(2-(4-fluorophenyl-1-yl)pyridinato-N,C$^{2'}$) platinum(II)

Chemical Formula 53: tris(2-(5-fluorophenyl-1-yl)pyridinato-N,C$^{2'}$) gold(III)

Chemical Formula 54: tris(2-(4-fluorophenyl-1-yl)benzo[c]quinolinato-N,C$^{2'}$) iridium(III)

Chemical Formula 55: tris(2-(4-cyanophenyl-1-yl)quinolinato-N,C$^{2'}$) iridium (III)

Chemical Formula 56: bis(2-(4-cyanophenyl-1-yl)benzothiazolato-N,C$^{2'}$)acetylacetonato iridium(III)

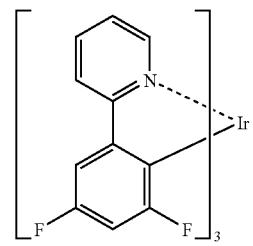

(Chem.Form.45)

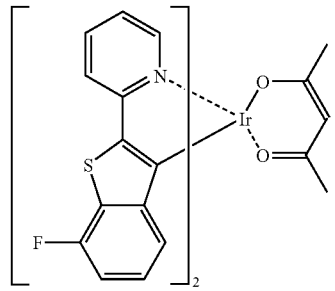

(Chem.Form.46)

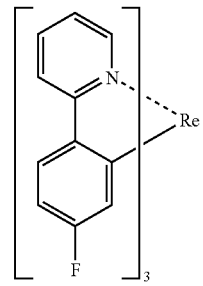

(Chem.Form.47)

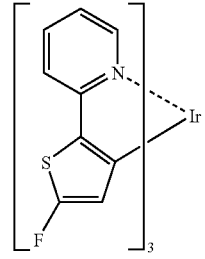

(Chem.Form.48)

-continued (Chem.Form.49)

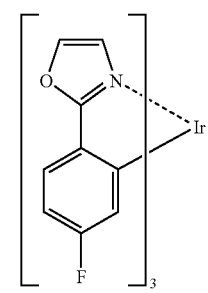

(Chem.Form.50)

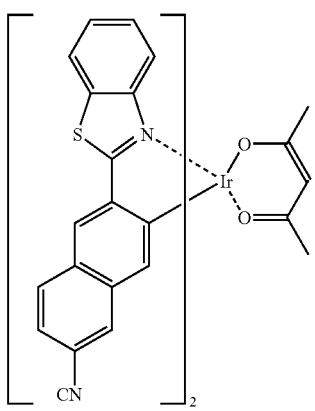

(Chem.Form.51)

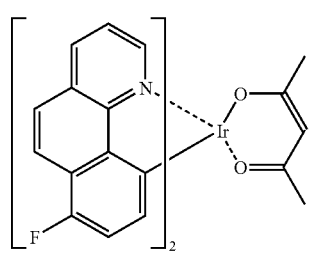

(Chem.Form.52)

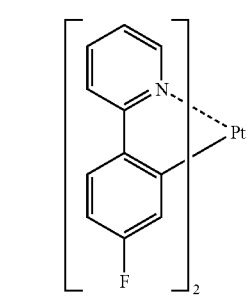

(Chem.Form.53)

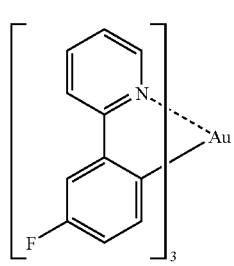

-continued (Chem.Form.54)

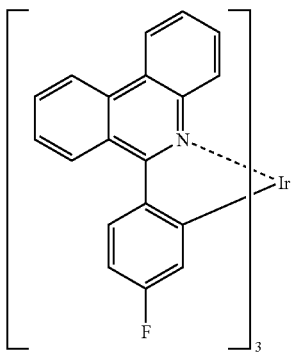

(Chem.Form.55)

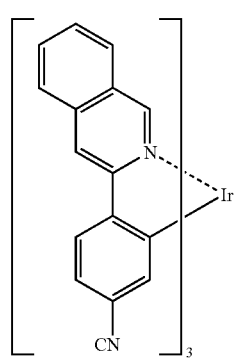

(Chem.Form.56)

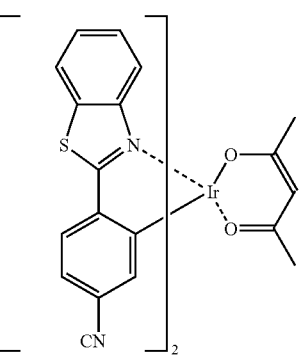

DESCRIPTION OF THE PREFERRED EMBODIMENTS

In the following, the present invention will be described more specifically by way of Examples, however, it is to be understood that the present invention is not limited to the following Examples but can be practiced with appropriate changes.

EXAMPLE 1

Synthesis of tris(2-(3,5-difluorophenyl-1-yl)-pyridinato-N,$C^{2'}$) iridium(III)

As a reaction vessel, a four neck flask of about 500 cm³ in volume, made of borosilicate glass was prepared (hereinafter, simply referred to as a reaction vessel), and a babbled shaped Allihn type water-cooling condenser tube of which cooling part is about 20 cm long (hereinafter, simply referred to as a condenser) was connected to the reaction vessel so as to ensure airtightness at the common taper joint. A mechanic-type stirrer made up of a motor, a joint, a glass stirring bar and a stirring blades of fluorine resin, and an airtight seal through which the stirring bar is penetrated were connected to a connection port on the top of the reaction vessel, so that efficient stirring of the contents in the reaction vessel was ensured while keeping the airtightness. An enclosure-type connection tube for introducing inert gas was connected to one of connection ports on the side of the reaction vessel, making it possible to introduce the inert gas into the upper space of the reaction vessel inside while keeping the airtightness. A glass canaliculus for blowing the inert gas into the contents of the reaction vessel was connected to the other of the connection ports on the side of the reaction vessel, making it possible blowing-in the inert gas to remove the dissolved oxygen in the contents while keeping the airtightness.

50 $cm^3$ of glycerol as a reaction solvent (hereinafter, simply referred to as a reaction solvent) was put in the reaction vessel, and nitrogen gas serving as the inert gas after removal of oxygen (hereinafter, simply referred to as inert gas) was blown into the reaction vessel through the glass canaliculi for about 15 minutes, to thereby remove the oxygen dissolved in the reaction solvent. The reaction solvent was gradually heated to 100° C. while blowing the inert gas to decrease the viscosity and the solubility of oxygen, to thereby highly remove the dissolved oxygen. Thereafter, the reaction solvent was cooled to the room temperature (about 25° C.) while introducing the inert gas from the connected tube.

While introducing the inert gas from the connected tube, 1 mmol of tris(acetylacetonato) iridium (III) serving as the above-mentioned first material was put into the reaction vessel and allowed to dissolve in the above-mentioned reaction solvent wherein the dissolved oxygen was highly removed. Thereafter, 3.5 mmol of (3,5-difluorophenyl-1-yl) pyridine serving as the above-mentioned second material was added while introducing the inert gas from the connected tube, was stirred for about 10 minutes at the room temperature, and was mixed sufficiently. This mixture was gently heated under stirring, reaction solvent was evaporated, condensed in the cooling tower, and kept heated for 10 hours while maintaining such a reflux condition. The temperature of the outer wall at the bottom of the reaction vessel at the time of reflux was about 295° C.

After slowly cooling this reaction mixture to about 30° C., 200 $cm^3$ of dilute hydrochloric acid aqueous solution in a concentration of 1 mol/L was added to thereby dissolve the above-mentioned second material remaining unreacted in the form of a chlorate. At this time, most part of the above-mentioned unreacted first material is also considered to be dissolved in the solution. As a pale yellow precipitation generates, the precipitation was collected by suction filtration. Furthermore, in order to remove impurities of higher solubility, after washing the precipitation on the filter with a small amount of methanol, the solvent was evaporated to obtain an objective organometallic compound.

As a result of the above-mentioned process, about 0.4 mmol of the objective organometallic compound was obtained (yield: about 40%). This compound was irradiated with an ultraviolet ray of about 370 nm in wavelength, and blue light emission was observed.

In order to purify the objective organometallic compound more, the compound was heated to about 300° C. under a vacuum of not more than 5 Pa to conduct sublimation purification. The loss due to the sublimation purification was about 50%, and a brown nonsublimable residue was observed. Atomic analysis of the purified compound after sublimation purification resulted in a composition that almost coincides with the expected composition.

EXAMPLE 2

Synthesis of bis(2-(7-fluorobenzothiophene-2'-yl)-pyridinato-N,$C^{2'}$)acetylacetonato iridium (III)

The reaction was conducted in the same manner as in Example 1 except that diethylene glycol as the reaction solvent, 1 mmol of iridium chloride (III) as the first material and 2.5 mmol of 2-(6-fluorobenzothiophene-2'-yl)pyridine as the second material were used, and an intermediate which is considered as a dinuclear complex of iridium was synthesized.

Next, the reaction was conducted in the same manner as in Example 1 except that a four neck flask of about 100 $cm^3$ in volume as the reaction vessel, diethylene glycol as the reaction solvent, 0.1 mmol of the above-mentioned intermediate as the first material, 0.25 mmol of acetyl acetone as the ligand, 110 mg of sodium carbonate as an absorber for leaving chlorine were used, and an objective organometallic compound was obtained. This compound was irradiated with an ultraviolet ray having a wavelength of about 370 nm, and then red light emission was observed. Atomic analysis of the compound after sublimation purification resulted in a composition that almost coincides with the expected composition.

EXAMPLE 3

Synthesis of tris(2-(4-fluorophenyl-1-yl)-pyridinato-N,$C^{2'}$) rhenium (III)

The reaction was conducted in the same manner as in Example 1 except that 1,3-dinitrobenzene as the reaction solvent, 1 mmol of rhenium chloride (III) as the first material, (4-fluorophenyl-1-yl)-pyridine as the second material were used, and an objective organometallic compound was obtained. This compound was irradiated with an ultraviolet ray having a wavelength of about 370 nm, and then blue light emission was observed. Atomic analysis of the substance after sublimation purification resulted in a composition that almost coincides with the expected composition.

EXAMPLE 4

Production and Evaluation of Light Emitting Device

On a glass substrate on which an anode made of $In_2O_3$—$SnO_2$ (ITO) was formed in advance, an organic thin film, followed by a cathode made of an alloy of indium and magnesium (Mg:In) was formed by way of the deposition under a vacuum on the order of $10^{-4}$ Pa, whereby a light emitting device was produced. Hereinafter, a process for forming the organic thin film will be explained in detail.

On the surface of the anode made of ITO, a layer made of 4,4,4-tris(3-methylphenylphenylamino)triphenyl amine(abbreviated as MTDATA, abbreviation will be made in the same manner below) shown by (Chemical Formula 57) which serves as a hole injection layer, and then a layer made of 4,4'-bis[N-(1-naphthyl)-N-phenyl-amino]biphenyl (NPB) shown by (Chemical Formula 58) which serves as a hole transporting layer were formed. Next, after forming a layer wherein 10% wt of tris(2-(3,5-difluorophenyl-1-yl)-pyridinato-N,$C^{2'}$) iridium (III) synthesized in Example 1 is mixed into 4,4'-bis(carbazole-9-yl)-biphenyl (CBP) shown by (Chemical Formula 59) as a mixture light emitting layer, a layer made of 2,9-dimethyl-4,7-diphenyl-1,10-phenanthroline (BCP) shown by (Chemical Formula 60) was formed as a hole blocking layer. Thereafter a layer made of aluminum tris(8-hydroxyquinoline) (Alq) shown by (Chemical Formula 61) was formed as an electron injection layer, and then a cathode made of a magnesium alloy including 10% wt of indium (Mg:In) was deposited to thereby produce the light emitting device.

(Chem.Form.57)

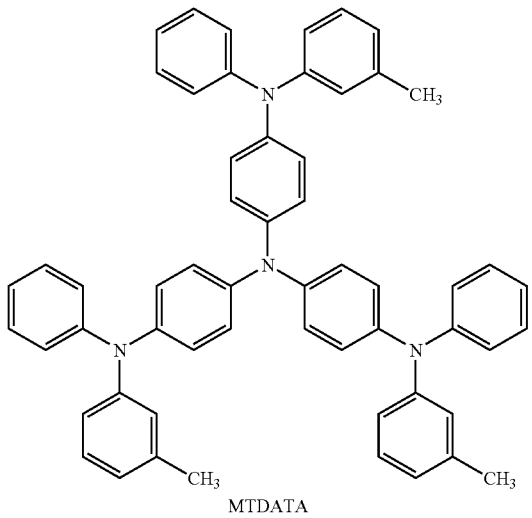

MTDATA (Chem.Form.58)

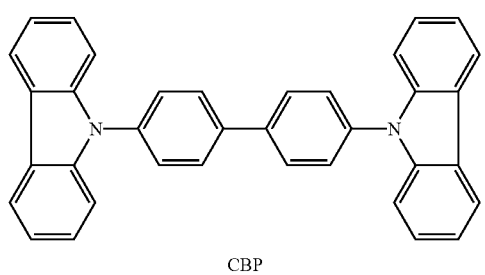

NPB (Chem.Form.59)

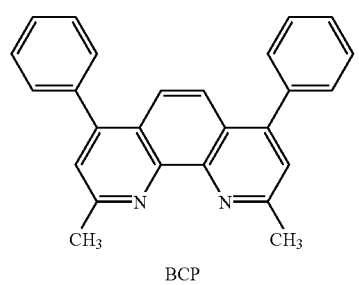

CBP (Chem.Form.60)

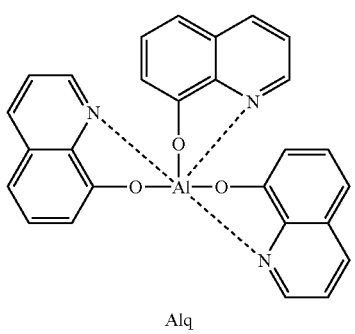

BCP

-continued (Chem.Form.61)

Alq

Film thickness of each layer measured by a quartz oscillator type film thickness gage is shown inside the parentheses in the following expression.

ITO/MTDATA (20 nm)/NPB (10 nm)/mixture light emitting layer (20 nm)/BCP (10 nm)/Alq (20 nm)/Mg:In (200 nm)

The simplified molecular formula of MTDATA was $C_{57}H_{48}N_4$ (the numbers in the simplified molecular formula represent the numbers of atoms in the molecule, which also applies in the following), the molar mass was 789.04 g/mol, the melting point was 203° C., the glass transition temperature was 75° C., the ionization potential was 5.1 eV, the energy gap between the highest occupied molecular orbital (HOMO) and the lowest unoccupied molecular orbital (LUMO) was 3.1 eV.

The simplified molecular formula of NPB was $C_{44}H_{32}N_2$, the molar mass was 588.75 g/mol, the melting point was 277° C., the glass transition temperature was 96° C., the ionization potential was 5.4 eV, and the energy gap between the HOMO and the LUMO was 3.1 eV.

The simplified molecular formula of BCP was $C_{26}H_{20}N_2$, the molar mass was 360.45 g/mol, the melting point was 279 to 283° C., the ionization potential was 6.7 eV, and the energy gap between the HOMO and the LUMO was 3.5 eV. It can be considered that it is difficult for holes to be injected into the BCP layer since the ionization potential of BCP is large, and thus the BCP acts as the hole blocking layer.

The simplified molecular formula of Alq was $C_{27}H_{18}N_3O_3Al$, the molar mass was 459.4318 g/mol, there was no melting point, the thermal cracking temperature was 412° C., the glass transition temperature was 175° C., the ionization potential was 5.7 eV, and the energy gap between the HOMO and the LUMO was 2.7 eV.

Upon energizing the above-mentioned light emitting device by application of DC voltage, blue light emission of 100 cd/m² in brightness was obtained, and the current-luminescence efficiency at this time was 3.1 cd/A. Since the brightness was almost in proportion with the current density, it was confirmed that the brightness could be very easily controlled.

EXAMPLE 5

Production and Evaluation of Light Emitting Device

A light emitting device was produced in the same manner as in Example 4 except that as the mixture light emitting layer, CBP mixed with 10% wt of bis(2-(6-fluorobenzothiophene-2'-yl)pyridinato-N,$C^{2'}$)acetylacetonato iridium (III) synthesized in Example 2 was used. Upon energizing this light emitting device by application of DC voltage, red light emission of 100 cd/m² in brightness was obtained, and the current-luminescence efficiency at this time was 3 cd/A. The brightness was almost in proportion with the current density.

EXAMPLES 6 TO 15 AND COMPARATIVE EXAMPLES 1 TO 12

Productions and Evaluations of Light Emitting Devices

Light emitting devices were produced in the same manner as in Example 4 except that as the mixture light emitting layer, CBP mixed with 10% wt of organometallic compounds listed shown in Table 1 was used. As shown in Table 1, in Examples 6 to 15, organometallic compounds having the structures shown by (Chemical Formula 47) to (Chemical Formula 56) were used. And in Comparative examples 1 to 12, organometallic compounds having the structures lacking substituent F or CN in the organometallic compounds shown by (Chemical Formula 45) to (Chemical Formula 56) were used.

The resultant light emitting devices were energized by application of DC voltage, and the luminous color and luminous efficiency at the brightness of 100 cd/m² are presented in Table 1. In Table 1, also the results of Examples 4 and 5 are presented.

EXAMPLES 16 TO 38 AND COMPARATIVE EXAMPLES 13 TO 17

Productions and Evaluations of Light Emitting Devices

Light emitting devices were produced in the same manner as in Example 4 except that CBP mixed with 10% wt of organometallic compounds listed in Table 2 and Table 3 were used as the mixture light emitting layer.

In Examples 16 to 38, organometallic compounds, which are M, s, Lb and t shown in Table 2 and Table 3 in the general formulas (23) to (28) were used. In ligand Lb, "acac" represents acetylacetonato ligand shown in the formula (29), "pic" represents picolinato ligand shown in the formula (30) and "CO" represents carbonyl ligand.

In Comparative examples 13 to 17, organometallic compounds having structures lacking the substituent $CF_3$ in Examples 17 to 21 were used.

The resultant light emitting devices were energized by application of DC voltage, and luminous color and luminous efficiency at the brightness of 100 cd/m² are presented in Table 2 and Table 3.

TABLE 1

| | Structure of Organometallic Compound | Luminous Color | Luminous Efficiency (cd/A) |
|---|---|---|---|
| Ex. 4 | Chemical Formula 45 | Blue | 3.1 |
| Comp. Ex. 1 | Structure Lacking Substituent F In Chemical Formula 45 | Green | 3.2 |
| Ex. 5 | Chemical Formula 46 | Red | 3 |
| Comp. Ex. 2 | Structure Lacking Substituent F In Chemical Formula 46 | Red | 1.5 |
| Ex. 6 | Chemical Formula 47 | Blue | 0.5 |
| Comp. Ex. 3 | Structure Lacking Substituent F In Chemical Formula 47 | Blue-Green | 0.2 |
| Ex. 7 | Chemical Formula 48 | Green | 2 |
| Comp. Ex. 4 | Structure Lacking Substituent F In Chemical Formula 48 | Green | 1.5 |
| Ex. 8 | Chemical Formula 49 | Green | 1.5 |
| Comp. Ex. 5 | Structure Lacking Substituent F In Chemical Formula 49 | Green | 1 |
| Ex. 9 | Chemical Formula 50 | Orange | 0.6 |
| Comp. Ex. 6 | Structure Lacking Substituent CN In Chemical Formula 50 | Yellow | 0.4 |
| Ex. 10 | Chemical Formula 51 | Green | 0.6 |
| Comp. Ex. 7 | Structure Lacking Substituent F In Chemical Formula 51 | Green | 0.5 |
| Ex. 11 | Chemical Formula 52 | Green | 0.15 |
| Comp. Ex. 8 | Structure Lacking Substituent F In Chemical Formula 52 | Green | 0.1 |
| Ex. 12 | Chemical Formula 53 | Green | 0.03 |
| Comp. Ex. 9 | Structure Lacking Substituent F In Chemical Formula 53 | Green | 0.01 |
| Ex. 13 | Chemical Formula 54 | Yellow | 0.3 |
| Comp. Ex. 10 | Structure Lacking Substituent F In Chemical Formula 54 | Yellow | 0.2 |
| Ex. 14 | Chemical Formula 55 | Yellow | 0.5 |
| Comp. Ex. 11 | Structure Lacking Substituent CN In Chemical Formula 55 | Yellow-Green | 0.4 |
| Ex. 15 | Chemical Formula 56 | Orange | 0.6 |
| Comp. Ex. 16 | Structure Lacking Substituent CN In Chemical Formula 56 | Yellow | 0.6 |

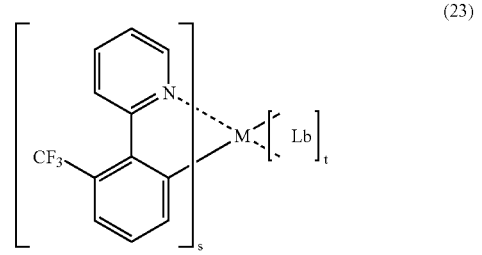

(23)

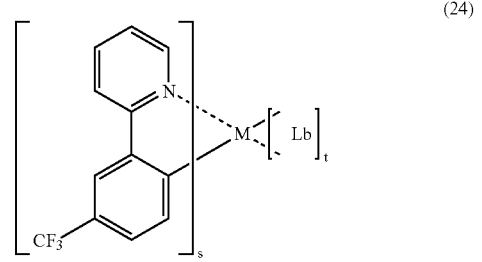

(24)

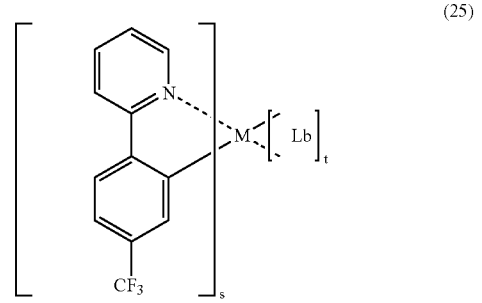

(25)

-continued

(26)
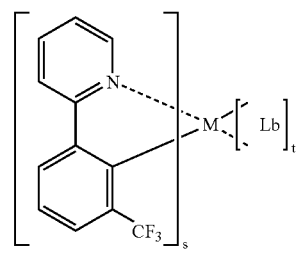

(27)
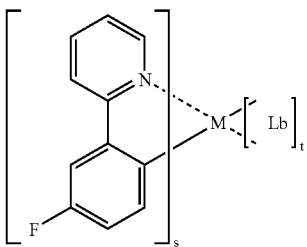

(28)
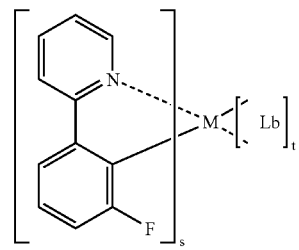

(29)
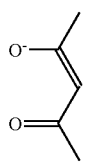

(30)
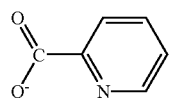

TABLE 2

| | Structure of Organometallic Compound | | | | Luminous Color | Luminous Efficiency (cd/A) |
|---|---|---|---|---|---|---|
| | General Formula | M | s | Lb | t | | |
| Ex. 16 | (23) | Ir | 3 | None | 0 | Blue | 5 |
| Ex. 17 | (23) | Ir | 2 | acac | 1 | Blue | 3.5 |
| Ex. 18 | (23) | Ir | 2 | pic | 1 | Blue | 4 |
| Ex. 19 | (23) | Ir | 1 | acac | 2 | Blue-Green | 0.01 |
| Ex. 20 | (23) | Ir | 1 | pic | 2 | Blue-Green | 0.01 |
| Ex. 21 | (23) | Re | 1 | CO | 4 | Green | 0.03 |
| Comp. Ex. 13 | Structure Lacking Substituent CF$_3$ In Example 17 | | | | | Green | 2.3 |
| Comp. Ex. 14 | Structure Lacking Substituent CF$_3$ In Example 18 | | | | | Green | 2.5 |
| Comp. Ex. 15 | Structure Lacking Substituent CF$_3$ In Example 19 | | | | | Green | 0.005 |
| Comp. Ex. 16 | Structure Lacking Substituent CF$_3$ In Example 20 | | | | | Green | 0.005 |

TABLE 2-continued

| | Structure of Organometallic Compound | | | | Luminous Color | Luminous Efficiency (cd/A) |
|---|---|---|---|---|---|---|
| | General Formula | M | s | Lb | t | | |
| Comp. Ex. 17 | Structure Lacking Substituent CF$_3$ In Example 21 | | | | | Green | 0.01 |

TABLE 3

| | Structure of Organometallic Compound | | | | Luminous Color | Luminous Efficiency (cd/A) |
|---|---|---|---|---|---|---|
| | General Formula | M | s | Lb | t | | |
| Ex. 22 | (24) | Ir | 3 | None | 0 | Blue | 4.5 |
| Ex. 23 | (24) | Ir | 2 | acac | 1 | Blue | 3 |
| Ex. 24 | (24) | Ir | 2 | pic | 1 | Blue | 3.5 |
| Ex. 25 | (25) | Ir | 3 | None | 0 | Blue | 3.7 |
| Ex. 26 | (25) | Ir | 2 | acac | 1 | Blue | 2.6 |
| Ex. 27 | (25) | Ir | 2 | pic | 1 | Blue | 2.8 |
| Ex. 28 | (26) | Ir | 3 | None | 0 | Blue | 2.9 |
| Ex. 29 | (26) | Ir | 2 | acac | 1 | Blue | 2.5 |
| Ex. 30 | (26) | Ir | 2 | pic | 1 | Blue | 2.6 |
| Ex. 31 | (27) | Ir | 3 | None | 0 | Blue-Green | 3.1 |
| Ex. 32 | (27) | Ir | 2 | acac | 1 | Green | 2.4 |
| Ex. 33 | (27) | Ir | 2 | pic | 1 | Blue-Green | 2.5 |
| Ex. 34 | (28) | Ir | 3 | None | 0 | Blue | 3 |
| Ex. 35 | (28) | Ir | 2 | acac | 1 | Blue-Green | 2.5 |
| Ex. 36 | (28) | Ir | 2 | pic | 1 | Blue | 2.6 |
| Ex. 37 | (23) | W | 2 | CO | 2 | Blue | 5.5 |
| Ex. 38 | (23) | W | 1 | CO | 4 | Blue | 3.6 |

According to the present invention, it is possible to provide an organometallic compound having an excellent luminous efficiency and capable of emitting red or blue light.

Also, a light emitting device according to the present invention can be rendered a full-color display apparatus or the like having an excellent luminous efficiency by including the luminescent organometallic compound according to the present invention into a light emitting layer.

What is claimed is:

1. A luminescent organometallic compound having the chemical structure represented by the following chemical formula (48):

(Chem. Form. 48)

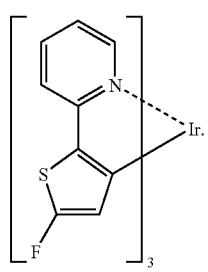

2. A light emitting device wherein a luminescent organometallic compound according to claim 1 is included in a light emitting layer arranged between a pair of electrodes.

* * * * *